(12) United States Patent
Cheng

(10) Patent No.: US 10,048,259 B2
(45) Date of Patent: Aug. 14, 2018

(54) PORTABLE FLUORESCENCE DETECTION SYSTEM

(71) Applicant: National Tsing Hua University, Hsinchu (TW)

(72) Inventor: Chao-Min Cheng, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 15/601,570

(22) Filed: May 22, 2017

(65) Prior Publication Data

US 2017/0254804 A1     Sep. 7, 2017

Related U.S. Application Data

(63) Continuation-in-part of application No. 14/757,476, filed on Dec. 23, 2015, now Pat. No. 9,689,869.
(Continued)

(30) Foreign Application Priority Data

Nov. 19, 2013   (TW) .............................. 102142015 A

(51) Int. Cl.
    *G01N 33/543*     (2006.01)
    *G01N 21/64*     (2006.01)
    (Continued)

(52) U.S. Cl.
    CPC ....... *G01N 33/54366* (2013.01); *G01N 21/01* (2013.01); *G01N 21/645* (2013.01);
    (Continued)

(58) Field of Classification Search
    CPC ............... G01N 21/6486; G01N 21/01; G01N 21/6454; G01N 21/6456; G01N 33/54366;
    (Continued)

(56) References Cited

U.S. PATENT DOCUMENTS 7,516,899 B2 *   4/2009   Laser ....................... G06K 7/12
                                                                235/454
7,796,266 B2     9/2010   Cohen et al.
(Continued)

FOREIGN PATENT DOCUMENTS

CN        102439422 A    5/2012
CN        202916197 U    5/2013
(Continued)

OTHER PUBLICATIONS

An Office Action from the corresponding Taiwanese application dated Feb. 15, 2016 is attached, 19 pages.
(Continued)

*Primary Examiner* — David Porta
*Assistant Examiner* — Faye Boosalis
(74) *Attorney, Agent, or Firm* — Muncy, Geissler, Olds & Lowe, P.C.

(57) ABSTRACT

A portable fluorescence detection system for a test unit comprises a housing, a light source module and a image capturing module. The housing has a receiving area for accommodating the test unit. The light source module is disposed in the housing and projecting light towards the receiving area. The image capturing module is disposed in the housing and receiving fluorescence light from the receiving area so as to capture an image. The above-mentioned system can be applied to the point-of-care testing.

19 Claims, 7 Drawing Sheets

Related U.S. Application Data which is a continuation of application No. 14/181,045, filed on Feb. 14, 2014, now Pat. No. 9,255,884.

(51) Int. Cl.
*G01N 21/01* (2006.01)
*H04W 4/80* (2018.01)
*H04W 4/00* (2018.01)

(52) U.S. Cl.
CPC ..... *G01N 21/6456* (2013.01); *G01N 21/6486* (2013.01); *G01N 33/54306* (2013.01); *H04W 4/00* (2013.01); *H04W 4/80* (2018.02); *G01N 2021/0137* (2013.01); *G01N 2021/6482* (2013.01); *G01N 2201/0221* (2013.01); *G01N 2201/061* (2013.01); *G01N 2201/062* (2013.01)

(58) Field of Classification Search
CPC ....... G01N 33/54306; G01N 2201/061; G01N 2021/0137; G01N 2021/6482
See application file for complete search history.

(56) References Cited

U.S. PATENT DOCUMENTS

| | | |
|---|---|---|
| 2010/0135857 A1 | 6/2010 | Hunter et al. |
| 2010/0141153 A1 | 6/2010 | Recker et al. |
| 2010/0249965 A1 | 9/2010 | Rao et al. |
| 2012/0157160 A1* | 6/2012 | Ozcan ................ G01N 21/6458 455/556.1 |

FOREIGN PATENT DOCUMENTS

| | | |
|---|---|---|
| CN | 203249870 U | 10/2013 |
| TW | 201015057 A | 4/2010 |
| TW | M455473 U | 6/2013 |
| TW | M465672 U | 11/2013 |

OTHER PUBLICATIONS

An Office Action from the corresponding CN Application No. 201410050123.6 dated Nov. 28, 2016, 10 pages.

Lo et al., "Portable Fluorescent Image Recording Device for Point-of-care Diagnosis," IEEE-Nanomed 2013 Conference, pp. 1-2 (Nov. 2013) with Conference information.

\* cited by examiner

PORTABLE FLUORESCENCE DETECTION SYSTEM

CROSS-REFERENCES TO RELATED APPLICATIONS

This application is a continuation-in-part of U.S. application Ser. No. 14/757,476 filed on Dec. 23, 2015, which is a continuation application of U.S. application Ser. No. 14/181,045 filed on Feb. 14, 2014 that claims the priority to Taiwan Patent Application No. 102142015 filed on Nov. 19, 2013.

BACKGROUND OF THE INVENTION

1. Field of the Invention

The present invention relates to a portable fluorescence detection system, and more particularly to the portable fluorescence detection system having a housing that receives a test unit, a light source device and an image capturing module for inspecting the test unit.

2. Description Of The Prior Art

The paper-based analysis device applied to clinical usage has been widely developed. For example, specific antigens, antibodies or nucleic acids can be monitored by the colorimetry or fluorescence signals. However, the colorimetry is limited by specific chemical reactions. While the sensibility and storage convenience of fluorescence strip are better than that of the colorimetry, such as the enzymatic analysis, the fluorescence analysis needs expensive and complex optical instruments. In this respect, the fluorescence analysis cannot be effectively and widely implemented to the field of the point-of-care testing (POCT). The point-of-care testing is not performed in the conventional laboratory but is performed at a location, such as a consulting room, an emergency room, a ward and a home environment, proximate to a patient. That is to say, the basic requirements for the point-of-care testing are economical, prompt and convenient.

According to the foregoing descriptions, the extremely desired goal to be achieved is to provide a portable fluorescence analysis system.

SUMMARY OF THE INVENTION

The present invention provides a portable fluorescence detection system for inspecting a test unit. The portable fluorescence detection system includes a housing for accommodating a light source module, an image capturing module and the test unit. Particularly, the light source module is disposed adjacent or opposite to the test unit and the image capturing module is utilized to capture the image of the test unit. Hence, the portable fluorescence detection system of this invention achieves the effects of being economical, prompt and convenient, and being adapted to the point-of-care testing.

Preferably, for effectively capturing and analyzing the image, the portable fluorescence detection system of the present invention takes advantage of the well-developed technologies in mobile electronic device and the wireless communication.

In one embodiment, the proposed portable fluorescence detection system comprises a housing, a light source module and an image capturing module. The test unit comprises a fluorescence probe for detecting an analyte within a specimen. The housing is non-transparent and has a receiving area for accommodating the test unit. The light source module is disposed in the housing opposite to the receiving area and projecting light towards the receiving area so as to excite the fluorescence probe to generate a fluorescent light. The image capturing module is disposed in the housing adjacent to the light source module and receiving fluorescence light from the receiving area so as to capture an image. The image capturing module and the light source module are able to wirelessly communicate with a processing module which is disposed away from the housing. In an alternative of the present embodiment, the light source is disposed on an interior surface of the housing between the receiving area and the image capturing module.

In another embodiment, the light source module and the image capturing module are integrated in a mobile electronic device, and the housing has an opening for attaching to the mobile electronic device so as to enclose the light source module, the image capturing module and the test unit.

In further another embodiment, the image capturing module is integrated in a mobile electronic device, and the housing has an opening for attaching to the mobile electronic device so as to enclose the image capturing module. The light source is disposed on an interior surface of the housing between the receiving area and the image capturing module. The light source module is able to wirelessly communicate with the mobile electronic device.

In yet another embodiment, the light source module and the image capturing module are disposed on the same side in the housing and the receiving area is located adjacent to the light source module, the portable fluorescence detection system further comprising a reflector disposed opposite to the light source module in the housing so as to reflect the fluorescence light generated from the test unit to the image capturing module.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENT

The detailed explanation of the present invention is described as follows. The described preferred embodiments are presented for purposes of illustrations and description, and they are not intended to limit the scope of the present invention.

Figure 1A:
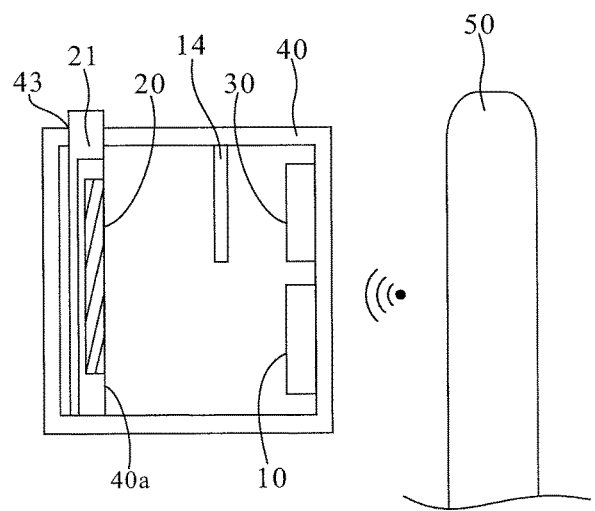
FIG. 1A is a schematic view illustrating the first embodiment of a portable fluorescence detection system according to the present invention.
Figure 1B:
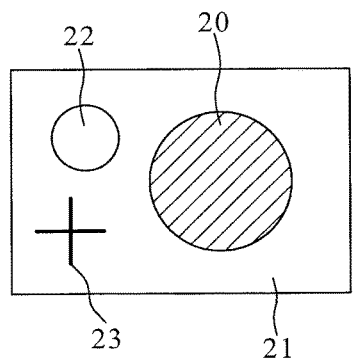
FIGS. 1B and 1C are schematic views illustrating two kinds of test units of the present invention.
Figure 1C:
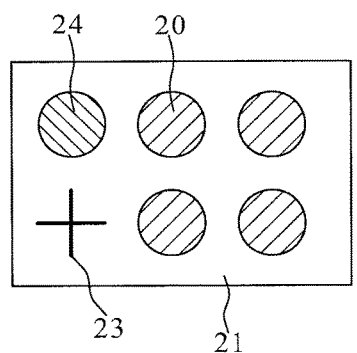

FIG. 1A shows the first embodiment of a portable fluorescence detection system of the present invention for inspecting a test unit 20. The portable fluorescence detection system comprises a light source module 10, a image capturing module 30 and a housing 40. In the present embodiment, the test unit 20 is formed on a strip 21 as shown in FIG. 1B. More specifically, the test unit 20 has a fluorescence probe fixed therein for detecting an analyte within a specimen, such as an antigen, an antibody, a nucleic acid or the like. It should be noted that the strip 21 may comprise a single test unit 20 (as shown in FIG. 1B) or a plurality of test units 20 (as shown in FIG. 1C). The fluorescence probes of the test units 20 in the strip 21 may be similar or different. For example, if the plurality of test units 20 comprise the same fluorescence probes, the strip 21 is adapted to detect the same kind of analyte in different specimens or is adapted to detect the same kind of analyte in a single specimen repeatedly at the same time. If the plurality of test units 20 comprise different fluorescence probes, the strip 21 is adapted to detect a plurality of types of analytes in a single specimen at the same time. The fluorescence detection by utilizing paper substrates can be accomplished by the presently known fluorescence detecting techniques, thus it is not further described herein.

The housing 40 has a receiving area 40a for accommodating the test unit 20. The housing 40 may be a non-transparent material or is configured to block external lights entering the interior of the housing 40 in a proper manner. A guide slot 43 may be formed on a side of the housing 40, so that the strip 21 with the test unit 20 can be directly inserted through the guide slot 43 so as to locate in the receiving area 40a. The light source module 10 is disposed in the housing 40 and projecting light towards the receiving area 40a where the test unit 20 located so as to excite the fluorescence probe to generate a fluorescent light. In the first embodiment as shown in FIG. 1A, the image capturing module 30 is disposed in the housing 40 opposite to the receiving area 40a for receiving fluorescence light from the receiving area 40a so as to capture an image. The light source module 10 is arranged adjacent to the image capturing module 30 and also opposite to the receiving area 40a. Preferably, the light source module 10 comprises at least one LED (Light Emitting Diode; not shown in the figures), and each test unit 20 is corresponding to at least one LED. In one embodiment, the light may be a UV-light, and the fluorescent light may be a visible light.

The portable fluorescence detection system further comprises a processing module (not shown in the figures). In the present embodiment, both of the image capturing module 30 and the light source module 10 are able to wirelessly communicate with the processing module which is disposed away from the housing 40, for example, in a mobile electronic device 50. In more detail, the image capturing module 30 comprises a first wireless communication unit (not shown) to transfer the image to the processing module. In the present embodiment, the fluorescence intensity of the fluorescence image is directly analyzed by the processing module installed in the mobile electronic device 50 such as a smart mobile phone or a tablet computer. It is noted that the manner of analyzing the fluorescence intensity of the fluorescence image is not limited. Alternatively, the fluorescence image can be transferred to a processing module which is disposed in a host. For the purpose of reducing the calculate loads of the mobile electronic device 50, it is also feasible for the mobile electronic device 50 transferring the fluorescence image to a host, such as a desktop computer or a remote server, to analyze the fluorescence image.

In the present embodiment, the light source module 10 comprises a second wireless communication unit (not shown) so that the light source module 10 is able to be controlled wirelessly. For example, the second wireless communication unit can be a Bluetooth module which enables the light source module 10 and the mobile electronic device 50 to perform wireless communication. Therefore, a user can control the light source module 10 through a user interface of the mobile electronic device 50. Through the user interface, the user can adjust the intensity of the light emitted from the light source module 10 or selectively activate at least one of a plurality of LEDs. In one embodiment, the image capturing module 30 and the light source module 10 may share the same wireless communication unit.

The content of analyte can be estimated by analyzing a fluorescence intensity of the image. For example, a curve graph comprising a known relationship between the content of analyte and the fluorescence intensity can be made in advance, so that the content of analyte can be obtained by referring to the detected fluorescence intensity and the curve graph. It should be noted that the relationship between the content of analyte and the fluorescence intensity may be positive relationship or negative relationship. That is to say, when the content of analyte is higher, the fluorescence intensity may be higher or lower. In one embodiment, analyzing the fluorescence intensity within a specific wavelength range is preferred. For example, a fluorescent light may comprise different light wavelength ranges of the red light, the green light and the blue light, but the content of analyte may simply have a remarkable relevance with the red light. In this case, the follow-up analysis can simply focus on analyzing the light intensity within the wavelength of the red light.

In general, the light emitted from the light source module 10 has a different light wavelength range from the fluorescent light. Referring to FIG. 1A, to prevent the light emitted from light source module 10 from interfering the image to be captured by the image capturing module 30, a filter 14 can be arranged in front of the image capturing module 30. The filter 14 filters out the light within the wavelength ranges of the light and only allows the fluorescent light to pass through so as to prevent the light from interfering the image to be captured and the corresponding analysis result. As the mentioned above, the content of the analyte may simply have a remarkable relevance with the light having a specific wavelength range. Therefore, the filter 14 can concurrently filter out the light and the light excluding a specific wavelength range of the fluorescent light so as to reduce the calculate loads for the subsequent image processing.

In one embodiment, the interior surface of the housing 40 is made of light absorbing material. The light absorbing material is adapted for absorbing the light emitted from the light source module 10 and/or the fluorescent light generated by the test unit 20, so that the lights reflected by the interior surface of the housing 40 is reduced and hence the quality of the fluorescence image is improved.

In general, when shooting or photographing within a close distance, the image capturing module 30 is not easy to focus.

Referring to FIGS. 1B and 1C, to focus easily, a focus area is arranged on the strip 21. For example, the focus area comprises a focus pattern 23. The focus pattern 23 assists the image capturing module 30 to focus so as to capture the fluorescence image in focus. For example, the focus pattern 23 comprises but not limited to a cross pattern and a stripe/checker pattern in black and white. In one embodiment, the focus pattern 23 comprises a fluorescence material, so that the focus pattern 23, under being excited, forms a fluorescence pattern to assists the image capturing module 30 to focus under the environment lacking of the light.

Referring to FIG. 1C, in one embodiment, the strip 21 comprises at least a control area 24. The control area 24 comprises a known amount of fluorescence material, so that when the control area 24 is excited, the control area 24 generates a fluorescent light with steady fluorescence intensity. Based on the fluorescence intensity generated from the control area 24, the image capturing module 30 can adjust an exposure value so as to capture the fluorescence image in a proper exposure value. Further, when analyzing the fluorescence intensity of the fluorescence image, the fluorescence intensity of the control area 24 is adapted to be a compensation basis so as to obtain more accurate analysis result.

As shown in FIG. 1B, in the first embodiment, the light source module 10 is further configured to provide a reference light, and the strip 21 has a hole 22 corresponding to the reference light. Under this arrangement, the image capturing module 30 can adjust an exposure value based on light intensity of the reference light so as to capture the fluorescence image in a proper exposure value. To prevent the reference light from being filtered out by the filter 14, in one embodiment, the center wavelength of the reference light is different from that of the light projecting toward the test unit 20. For example, the LED of the light source module 10 emits light to excite the fluorescence probe to generate fluorescent light. Another LED emits the reference light, and the image capturing module 30 senses the reference light via the hole 22 of the strip 21 to adjust the exposure value. It is understood that when analyzing the fluorescence intensity of the fluorescence image, the area corresponding to the reference light is adapted to be a compensation basis so as to obtain more accurate analysis result.

Figure 1D:
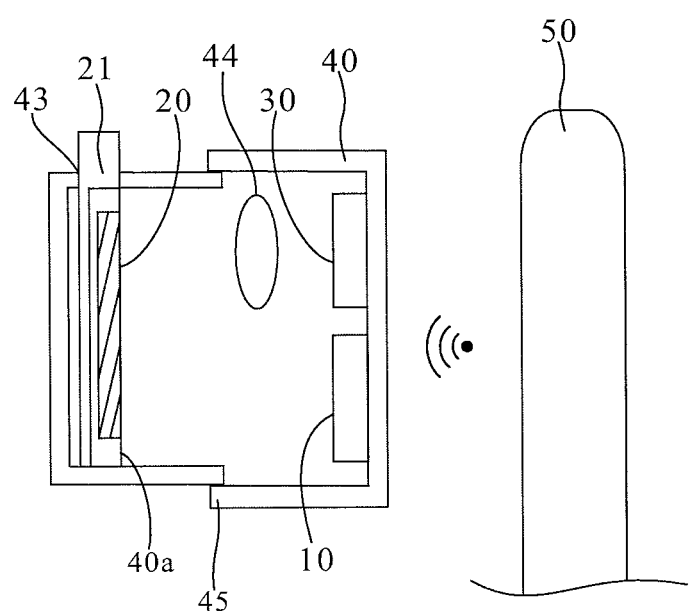
FIGS. 1D, 1E and 1F are schematic views illustrating other embodiments of the portable fluorescence detection system according to the present invention.
Figure 1E:
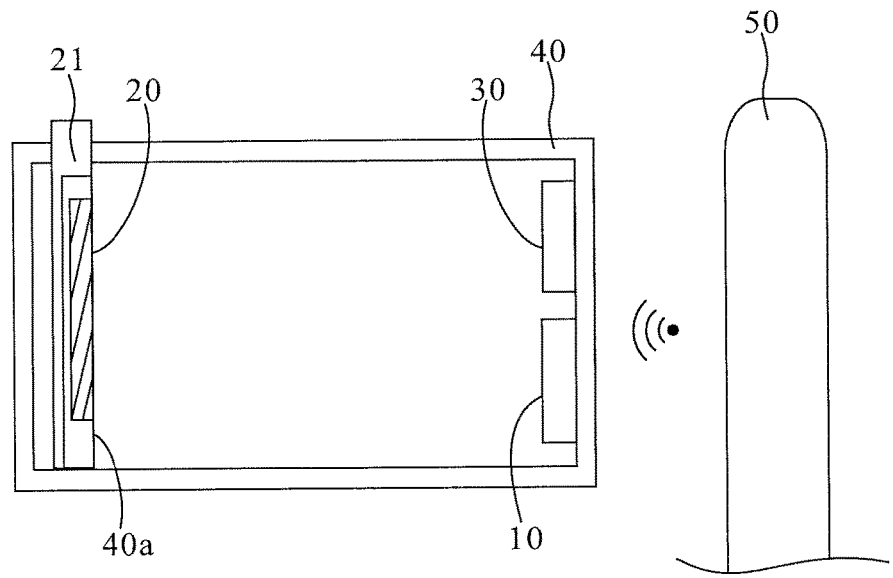
Figure 1F:
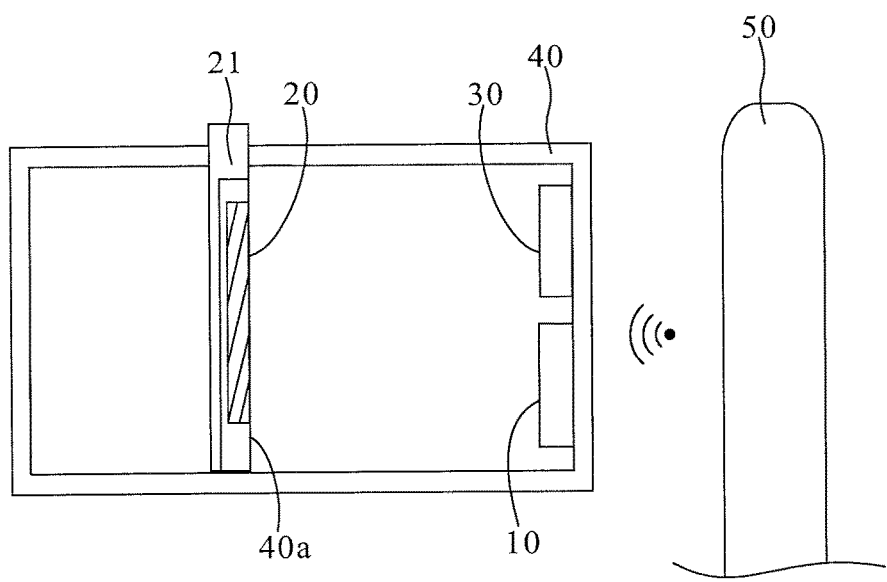

FIG. 1D shows another type of the first embodiment. The portable fluorescence detection system further comprises a lens 44 arranged between the receiving area 40a and the image capturing module 30. The housing 40 further comprises a focus adjusting mechanism 45 to adjust the distance between the test unit 20 and the image capturing module 30. Referring to FIGS. 1E and 1F, for example, the housing 40 provides a guide rail (not shown) parallel to the direction of the light axis of the image capturing module 30, and the strip 21 is movable along the guide rail. Under this arrangement, the strip 21 is movable along the direction of the light axis of the image capturing module 30 so as to adjust the distance between the test unit 20 and the image capturing module 30. Thus, through a user manually adjusting the focus of the image capturing module 30 via the user interface of the mobile electronic device 50, or through the assistance of the lens 44, the focus adjusting mechanism 45 and the focus pattern 23, a fluorescence image in focus is obtained.

Figure 2:
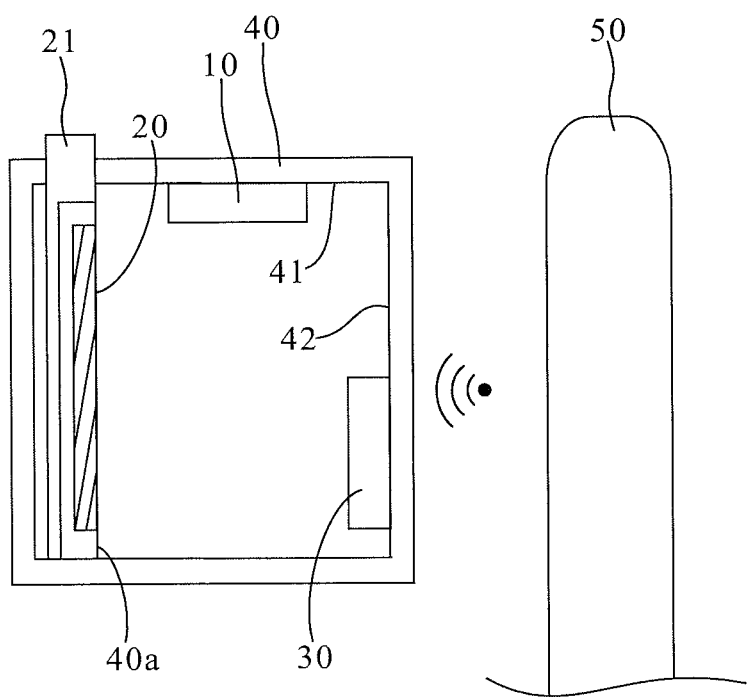
FIG. 2 is a schematic view illustrating the second embodiment of the portable fluorescence detection system according to the present invention.

FIG. 2 shows the second embodiment of a portable fluorescence detection system of the present invention for inspecting a test unit 20. This embodiment is similar to the appearance of the first embodiment. The difference between the first embodiment and the present embodiment is that the light source module 10 is disposed on an interior surface of the housing 40 between the receiving area 40a and the image capturing module 30. In more detail, the light source module 10 is disposed on a first interior surface 41 of the housing 40, and the image capturing module 30 is disposed on a second interior surface 42 of the housing 40.

Figure 3:
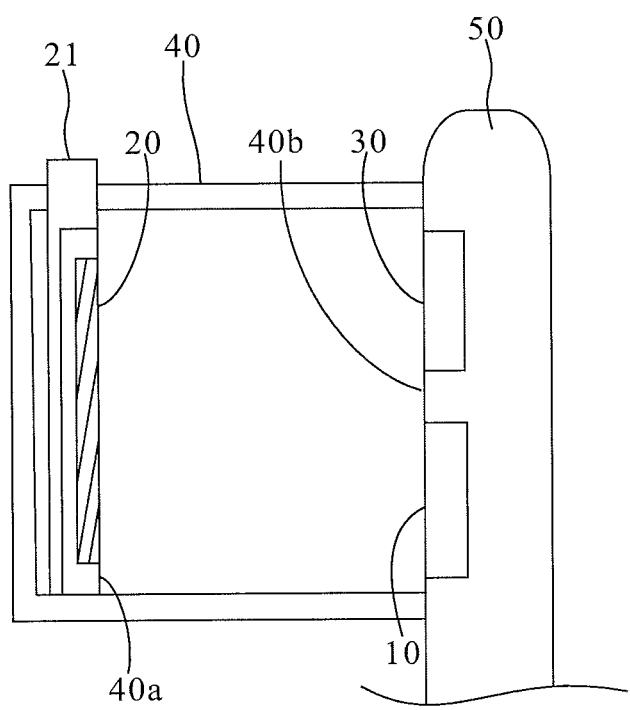
FIG. 3 is a schematic view illustrating the third embodiment of the portable fluorescence detection system according to the present invention.

FIG. 3 shows the third embodiment of a portable fluorescence detection system of the present invention for inspecting a test unit 20. The present embodiment discloses a light source module 10, a image capture module 30 and a housing 40 which are also disclosed in the first embodiment. The housing 40 has a receiving area 40a for the test unit 20 being disposed therein. The light source module 10 is enclosed in the housing 40 for projecting light towards the receiving area 40a. The image capturing module 30 is also enclosed in the housing 40 for receiving fluorescence light from the receiving area 40a so as to capture an image. The difference between the first embodiment and the present embodiment is that the light source module 10 and the image capturing module 30 of the present embodiment are integrated in the mobile electronic device 50 and the light source module 10 is disposed adjacent to the image capturing module 30. The housing 40 has an opening 40b for attaching to the mobile electronic device 50 so as to enclose the light source module 10 and the image capturing module 30.

Figure 4:
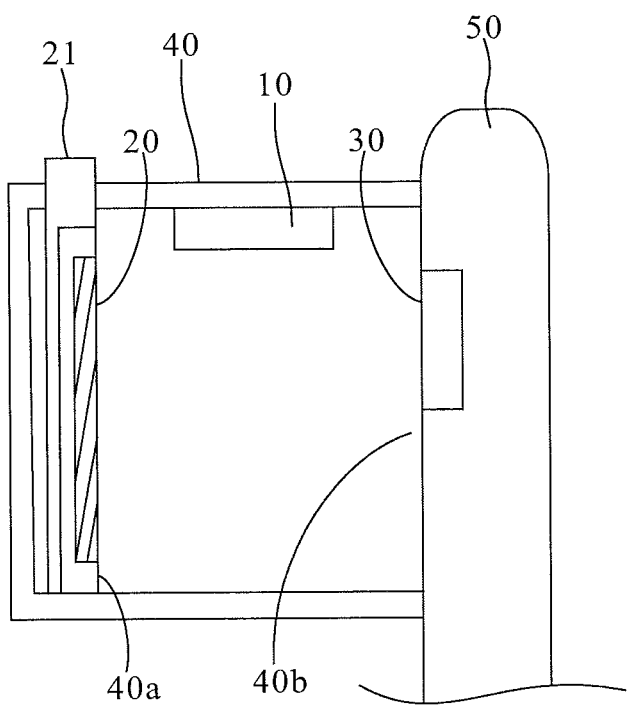
FIG. 4 is a schematic view illustrating the forth embodiment of the portable fluorescence detection system according to the present invention.

FIG. 4 shows the forth embodiment of a portable fluorescence detection system of the present invention for inspecting a test unit 20. The present embodiment discloses a light source module 10, an image capture module 30 and a housing 40 which are also disclosed in the third embodiment. The housing 40 has a receiving area 40a for the test unit 20 being disposed therein. The light source module 10 is disposed in the housing 40 for projecting light towards the receiving area 40a. The image capturing module 30 is enclosed in the housing 40 to receive fluorescence light from the receiving area 40a so as to capture an image. The difference between the third embodiment and the present embodiment is that the image capturing module 30 is integrated in the mobile electronic device 50, and the housing 40 has an opening 40b for attaching to the mobile electronic device 50 so as to enclose the image capturing module 30. The light source module 10 is disposed on an interior surface of the housing 40 between the receiving area 40a and the image capturing module 30, and the light source module 10 has a wireless communication unit so that the light source module 10 is able to be controlled wirelessly by the mobile electronic device 50.

Figure 5:
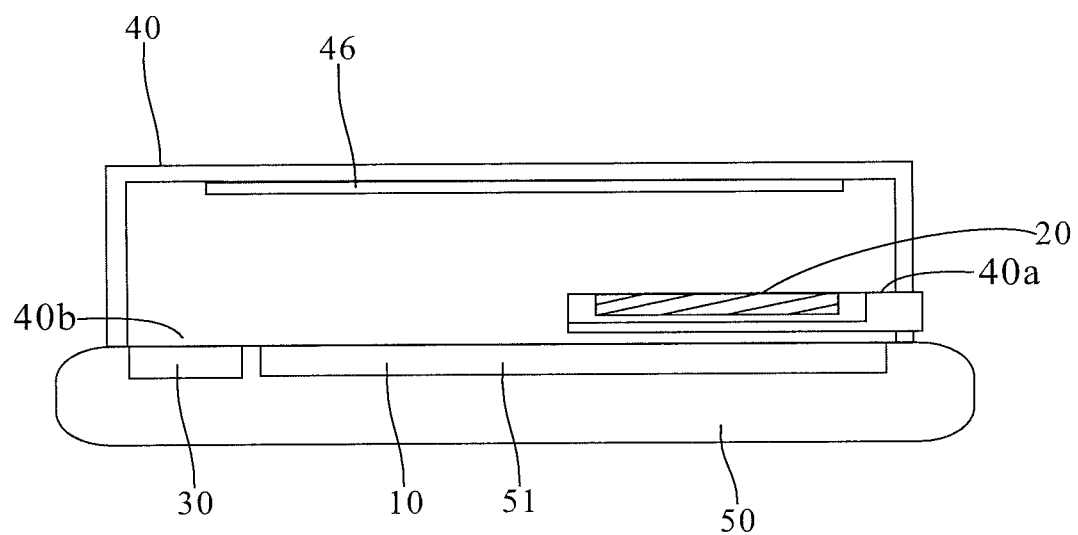
FIG. 5 is a schematic view illustrating the fifth embodiment of the portable fluorescence detection system according to the present invention.

FIG. 5 shows the fifth embodiment of a portable fluorescence detection system of the present invention for inspecting a test unit 20. The present embodiment discloses a light source module 10, an image capture module 30, a housing 40 and a reflector 46. The light source module 10 and the image capturing module 30 are disposed on the same side in the housing 40 and a receiving area 40a of the housing 40 is located adjacent to the light source module 10. The housing 40 has an opening 40b for attaching to the mobile electronic device 50 so as to enclose the light source module 10 and the image capturing module 30. In the present embodiment, the light source module 10 and the image capturing module 30 are integrated in the mobile electronic device 50. The reflector 46 is disposed on an interior surface of the housing 40 opposite to the light source module 10 in the housing 40 so as to reflect the fluorescence light to the image capturing module 30. In more detail, the light source module 10 is the screen 51 of the mobile electronic device. The test unit 20 is disposed on the screen 51 so that light emitted by the screen 51 irradiates on the test unit 20 to generate a fluorescent light.

To summarize the foregoing descriptions, the portable fluorescence detection system of the present invention is configured to install the light source module beside or opposite to the test unit 20 so as to project light towards the test unit 20. The portable fluorescence detection system of the present invention takes advantage of the technologies in mobile electronic device and the wireless communication. In other words, the portable fluorescence detection system of the present invention is adapted to perform a fluorescence test without the need for any expensive or complex optical instrument. Therefore, the portable fluorescence detection system of the present invention costs far below the conventional fluorescence analysis system and having a benefit of being applied to the field of the point-of-care testing.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A portable fluorescence detection system for inspecting a test unit, the portable fluorescence detection system comprising:
    a housing having a receiving area for accommodating the test unit;
    a light source module being disposed in the housing and projecting light towards the receiving area, and the light source module comprising a second wireless communication unit so that the light source module is able to be controlled wirelessly; and
    an image capturing module being disposed in the housing and receiving fluorescence light from the receiving area so as to capture an image.

2. The portable fluorescence detection system as claimed in claim 1, wherein the image capturing module is disposed opposite to the receiving area.

3. The portable fluorescence detection system as claimed in claim 2, wherein the light source module is disposed adjacent to the image capturing module and opposite to the receiving area.

4. The portable fluorescence detection system as claimed in claim 3, wherein the light source module and the image capturing module are integrated in a mobile electronic device, and the housing has an opening for attaching to the mobile electronic device so as to enclose the light source module and the image capturing module.

5. The portable fluorescence detection system as claimed in claim 3, further comprising a processing module which is disposed away from the housing wherein at least one of the image capturing module and the light source module is able to wirelessly communicate with the processing module.

6. The portable fluorescence detection system as claimed in claim 5, wherein the image capturing module comprises a first wireless communication unit to transfer the image to the processing module.

7. The portable fluorescence detection system as claimed in claim 5, wherein the processing module is integrated in a mobile electronic device.

8. The portable fluorescence detection system as claimed in claim 2, wherein the light source is disposed on an interior surface of the housing between the receiving area and the image capturing module.

9. The portable fluorescence detection system as claimed in claim 8, wherein the image capturing module is integrated in a mobile electronic device, and the housing has an opening for attaching to the mobile electronic device so as to enclose the image capturing module.

10. The portable fluorescence detection system as claimed in claim 8, wherein at least one of the image capturing module and the light source module is able to wirelessly communicate with a processing module which is disposed away from the housing.

11. The portable fluorescence detection system as claimed in claim 10, wherein the image capturing module comprises a first wireless communication unit to transfer the image to the processing module.

12. The portable fluorescence detection system as claimed in claim 10, wherein the processing module is integrated in a mobile electronic device.

13. The portable fluorescence detection system as claimed in claim 2, further comprising a lens arranged between the receiving area and the image capturing module.

14. The portable fluorescence detection system as claimed in claim 2, wherein the housing comprises a focus adjusting structure for adjusting a distance between the receiving area and the image capturing module.

15. The portable fluorescence detection system as claimed in claim 1, wherein the light source module and the image capturing module are disposed on the same side in the housing and the receiving area is located adjacent to the light source module, the portable fluorescence detection system further comprising a reflector disposed opposite to the light source module in the housing so as to reflect the fluorescence light to the image capturing module.

16. The portable fluorescence detection system as claimed in claim 1, wherein the test unit comprises a fluorescence probe for detecting an analyte within a specimen.

17. The portable fluorescence detection system as claimed in claim 1, further comprising a filter disposed in the housing for passing a specific wavelength range of light.

18. The portable fluorescence detection system as claimed in claim 1, wherein an interior surface of the housing is made of light absorbing material.

19. The portable fluorescence detection system as claimed in claim 1, wherein the light source module further provides a reference light.

\* \* \* \* \*